(12) United States Patent
Bukhari

(10) Patent No.: US 10,881,983 B2
(45) Date of Patent: Jan. 5, 2021

(54) METHOD FOR EXTRACTION OF ETHYL MALTOL FROM PASSION FLOWER

(71) Applicant: THE WINNING COMBINATION, Winnipeg (CA)

(72) Inventor: Shazad Bukhari, Winnipeg (CA)

(73) Assignee: The Winning Combination, Winnipeg (CA)

( * ) Notice: Subject to any disclaimer, the term of this patent is extended or adjusted under 35 U.S.C. 154(b) by 0 days.

(21) Appl. No.: 16/686,767

(22) Filed: Nov. 18, 2019

(65) Prior Publication Data

US 2020/0086231 A1    Mar. 19, 2020

Related U.S. Application Data

(60) Provisional application No. 62/902,039, filed on Sep. 18, 2019.

(51) Int. Cl.

| | |
|---|---|
| *B01D 11/02* | (2006.01) |
| *C07D 309/22* | (2006.01) |
| *B01D 15/34* | (2006.01) |
| *B01D 15/12* | (2006.01) |
| *A61K 31/351* | (2006.01) |
| *A61K 36/00* | (2006.01) |

(52) U.S. Cl.
CPC ........ *B01D 11/0288* (2013.01); *A61K 31/351* (2013.01); *A61K 36/00* (2013.01); *B01D 15/12* (2013.01); *B01D 15/34* (2013.01); *C07D 309/22* (2013.01); *A61K 2236/15* (2013.01); *A61K 2236/17* (2013.01); *A61K 2236/33* (2013.01); *A61K 2236/333* (2013.01)

(58) Field of Classification Search
CPC . B01D 11/02; B01D 11/0288; B01D 11/0292; B01D 15/34; B01D 15/12; C07D 309/22; A61K 31/351; A61K 2236/33; A61K 2236/333; A61K 2236/30; A61K 2236/15; A61K 2236/17; A61K 36/00
See application file for complete search history.

(56) References Cited

U.S. PATENT DOCUMENTS

| | | | | |
|---|---|---|---|---|
| 4,311,691 | A * | 1/1982 | Fichera | A61K 8/498 131/270 |
| 5,939,565 | A * | 8/1999 | Jumppanen | C07D 309/40 549/418 |
| 6,156,291 | A * | 12/2000 | Pang | G01N 33/94 424/9.2 |
| 2011/0135774 | A1* | 6/2011 | Gesztesi | A61K 8/498 424/774 |

(Continued)

OTHER PUBLICATIONS

Dhawan et al. Anti-anxiety studies on extracts of Passiflora incarnata Linneaus. Journal of Ethnopharmacology 78 (2001) 165-170 (Year: 2001).*

(Continued)

*Primary Examiner* — Katherine Zalasky McDonald
(74) *Attorney, Agent, or Firm* — Michael R Williams; Ryan W Depuis; Ade & Company Inc

(57) ABSTRACT

A method for the extraction of natural ethyl maltol from passionflower plants is described. The plant material is extracted with a methanol based solvent and the natural ethyl maltol is recovered by column purification using a size exclusion purification column.

6 Claims, 5 Drawing Sheets

(56) References Cited

U.S. PATENT DOCUMENTS

2015/0044306 A1* 2/2015 Mitchell ............ B01D 11/0261
424/728

OTHER PUBLICATIONS

GoldBio, "Demystifying material grades for your laboratory," available at <https://www.goldbio.com/articles/article/demystifying-material-grades-for-your-laboratory>, available Jul. 27, 2016. (Year: 2016).*

Aoyagi et al. Studies on passiflora incarnata dry extract. I Isolation of maltol and pharmacological action of maltol and ethyl maltol. Chem. Pharm. Bull. 22(5) 1008-1013 (1974). (Year: 1974).*

Dos Santos et al. Sedative and Anxiolytic Effects of Methanolic Extract from the Leaves of Passiflora actinia. Brazilian Archives of Biology and Technology. vol. 49, n. 4 : pp. 565-573, Jul. 2006. (Year: 2006).*

Ingale et al. Pharmacological studies of *passiflora* sp. and their bioactive compounds. African Journal of Plant Science vol. 4(10), pp. 417-426, Oct. 2010. (Year: 2010).*

Sasidharan et. al. Extraction, Isolation and Characterization of Bioactive Compounds From Plants' Extracts. Afr J Tradit Complement Altern Med. (2011) 8(1):1-10. (Year: 2011).*

Silva et al. Analyses of Passiflora Compounds by Chromatographic and Electrophoretic Techniques. Critical Reviews in Analytical Chemistry (2015) 45, 76-95. (Year: 2015).*

Patel et al. Passiflora incarnata Linn: A phytopharmacological review. International Journal of Green Pharmacy, Oct.-Dec. 2009, p. 277-280. (Year: 2009).*

* cited by examiner

METHOD FOR EXTRACTION OF ETHYL MALTOL FROM PASSION FLOWER

PRIOR APPLICATION INFORMATION

The instant application claims the benefit of U.S. Provisional Patent Application 62/902,039, filed Sep. 18, 2019 and entitled "METHOD FOR EXTRACTION OF ETHYL MALTOL FROM PASSION FLOWER".

BACKGROUND OF THE INVENTION

*Passiflora*, known also as the passion flowers or passion vines, is a genus of about 550 species of flowering plants, the type genus of the family Passifloraceae.

Passion flower was not previously known to contain detectable amounts of ethyl maltol.

Ethyl maltol is related to the more common compound maltol in that the methyl group present in maltol is replaced with an ethyl group.

Specifically, the compounds 3-hydroxy-2-methyl-4-pyrone (maltol) and 3-hydroxy-2-ethyl-4-pyrone (ethyl maltol) are known for enhancing certain food flavors when present in small amounts.

U.S. Pat. No. 4,311,691 teaches a composition comprising a gamma pyrone such as maltol or ethyl maltol and an inert carrier capable of providing sustained release of the gamma pyrone in the mouth that is useful for inhibiting tobacco smoking.

SUMMARY OF THE INVENTION

According to a first aspect of the invention, there is provided a method for ethyl maltol extraction comprising:
  drying passionflower plant parts;
  grinding the dried passionflower plant parts into a powder;
  extracting the powder with a methanol solvent; and
  isolating ethyl maltol from the methanol solvent by column purification.

The column purification may be carried out with a size exclusion chromatographic column.

The column material in the size exclusion chromatographic column may have a diameter of about 60 Angstroms.

The methanol solvent may be selected from the group consisting of: dried methanol; 90:10 methanol:water; and methanol. The methanol may be HPLC grade methanol.

The passionflower plant parts may be herb tops.

DESCRIPTION OF THE PREFERRED EMBODIMENTS

Figure 1:
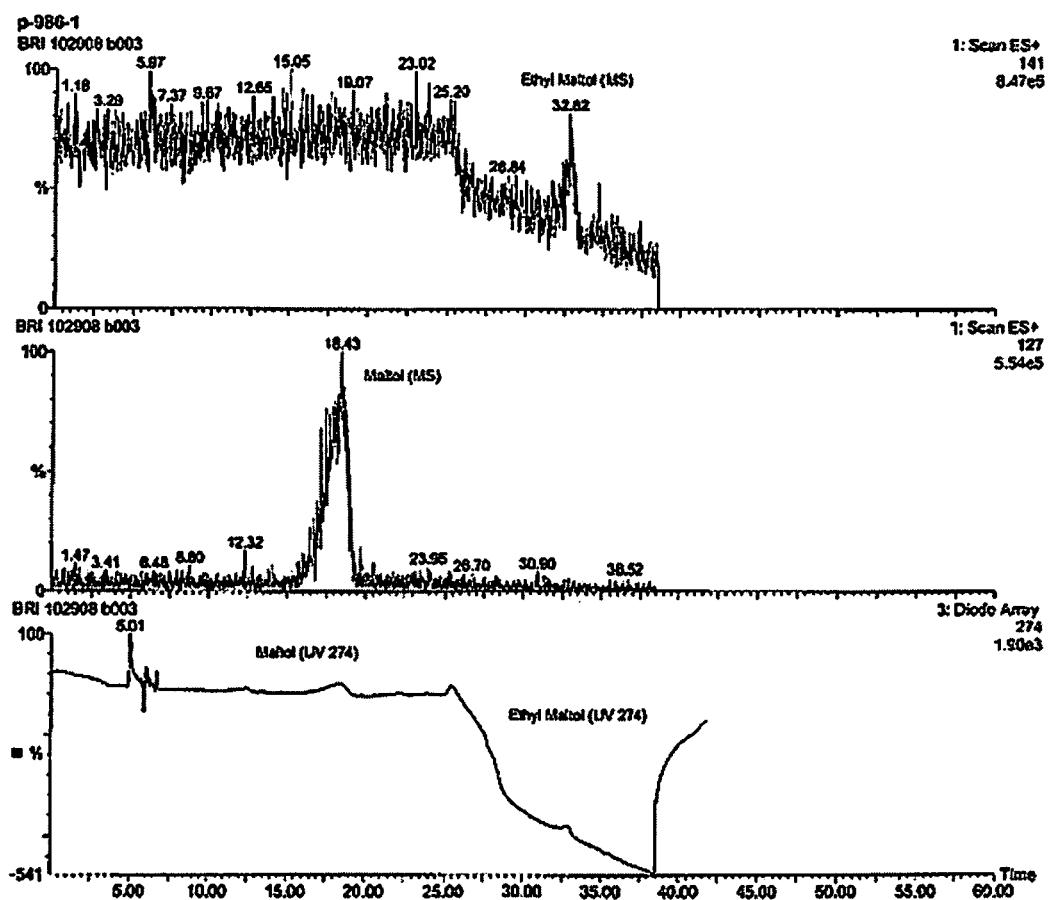
FIG. 1. LC/MS selected-ion chromatogram of the ethyl maltol reference standard sample (P-986-1) showing a protonated molecular ion [M+H] of 141 m/z (top), maltol at a protonated molecular ion [M+H] of 127 m/z (middle), and UV 274 nm chromatogram of the same reference standard sample (bottom).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method for extracting naturally occurring ethyl maltol from passionflower with a methanol-based solvent. Also described are methods for the elution/isolation thereof and for identification/confirmation of the isolated ethyl maltol.

As used herein, "isolating" or "isolated" refers to the separation of the compound of interest, in this case, ethyl maltol, from other components within the plant material and/or plant cells. As such, "isolated" does not necessarily mean "purified" but rather refers to an increase in concentration of the compound of interest by at least 10 fold, for example, at least 100 fold or more.

In one aspect of the invention, aerial parts or above ground parts or the herb top of the passionflower plant is collected, dried and powdered.

This starting material was then extracted with a polar solvent. In some embodiments, the polar solvent is a methanol-based solvent. In yet other embodiments, the methanol-based solvent is selected from the group consisting of: dried methanol; 90:10 methanol:water; and methanol. The methanol may be HPLC grade methanol. Other extraction solvents were tried and were unsuccessful.

The ethyl maltol was then isolated by column purification and recovered. In some embodiments of the invention, the ethyl maltol was purified on a size exclusion column. In some embodiments, the size exclusion material has an opening of approximately 60 Angstroms. In yet other embodiments, the column material is Silica Gel 60.

The invention will now be further explained and/or elucidated by way of examples; however, the invention is not necessarily limited to or by the examples.

Example 1—Methanol Extraction

HPLC grade Methanol (I liter) was dried by heating with Anhydrous Sodium Sulfate (20 gms) for 2 hours & filtered at the time of use. Passion Flower Powder (24.2 gms) was extracted by refluxing with dried methanol (250 mL) for 4 hours. Cooled, filtered and approximately 50 ml of extract was filtered through a mini column packed with Silica Gel 60. The filtrate thus obtained was labeled as 15165-(M-S-2).

Example 2—Methanol:Water Extraction

Passion Flower Powder Sample (28.4 gms) was extracted by refluxing with MeOH:Water::90:10 (250 mL) for approximately 4 hours. The extract was cooled, filtered and approximately 50 ml was filtered through a mini column packed with Silica Gel 60. The filtrate thus obtained was labeled as 15165.

Example 3—Methanol Extraction

Passion Flower Powder sample (26.1 gms) was also extracted by renuxing for 4 hours with HPLC grade Methanol (250 mL). The extract was cooled, filtered and approximately 50 ml was filtered through mini column packed with Silica Gel 60. This filtrate was labeled as 15165-(MeOH—S-2).

Example 4—Chromatograms Results

HPLC Conditions:
HPLC: Water's 2695 Alliance HPLC equipped with 996 Photo Diode Array Detector.
Column Used: Gemini 5 um, C18 (4.6×250 mm) column from Phenomex.
Column Temperature: 35 degrees centigrade
Sample Compartment Temperature: 25 degrees centigrade
Mobile phase:
MeOH: (W:1% HCl::990:10)::15:85 from 0 min to 25.0 min @ 0.5 ml/min;
& 1 ml/min from 25.5 min to 52.0 min;
MeOH: (W:1% HCl::990:10)::35:65 from 52.5 min to 75.0 min @ 1.6 ml/min;
MeOH:CAN::50:50 @ 2 ml/min from 80 to 85 min;
MeOH: (W:1% HCl::990:10)::15:85 @ 2 ml/min from 86 to 99.0 min;
& 99.0 min to 99.5 min @ 0.5 ml/min.
Monitoring wavelength: 210-400
Samples were injected for 105 mins and ethyl maltol was detected at 274 nm and 276 nm.
Ethyl maltol calibration curve was drawn by injecting 3, 4 and 6 ul of reference standard containing Maltol and Ethyl Maltol (concentration—2 ug/ml each)

Reference standard solutions containing Maltol & Ethyl Maltol (2 ug/ml each) was injected onto HPLC. Maltol eluted at 18.147 minutes and ethyl maltol eluted at 34.116 minutes. Ethyl Maltol was detected al 274 & 276 nm.

A compound present in sample extract 15165-(M-S-2) eluting at 34.057 mins was identified as Ethyl Maltol. Spectra of this identified compound present in sample was identical to the spectra of the Ethyl Maltol reference standard.

A compound present in sample extract 15165, eluting at 34.055 mins, was identified as Ethyl Maltol.

Example 5—LC/MS Data Summary

Electrospray LC/MS data was obtained from the ethyl maltol reference standard sample by acquiring molecular ion data over the mass range from 50 to 500 m/z throughout the chromatographic analysis time of 45 minutes. A representative LC/MS selected-ion chromatogram of the ethyl maltol reference standard sample, P-986-1, showing a protonated molecular ion [M+H]$^+$ of 141 m/z, is presented in FIG. 1. Maltol was also observed from the same reference standard sample at a molecular ion [M+H]$^+$ of 127 m/z. An HPLC ultraviolet detection chromatogram of the reference standard sample, P-986-1, was also simultaneously recorded at UV 274 nm.

| HPLC Gradient: | | | | |
|---|---|---|---|---|
| Time | Solvent A Methanol % | Solvent B Acetonitrile % | Solvent C 1% HCl in water | Flow Rate (ml/min) |
| 0.0 | 15 | 0 | 85 | 0.5 |
| 25.0 | 15 | 0 | 85 | 0.5 |
| 25.5 | 15 | 0 | 85 | 1.0 |
| 40.0 | 35 | 0 | 65 | 1.6 |
| 41.0 | 50 | 50 | 0 | 2.0 |
| 50.0 | 50 | 50 | 0 | 2.0 |
| 59.0 | 15 | 0 | 85 | 2.0 |
| 60.0 | 15 | 0 | 85 | 0.5 |

Figure 2:
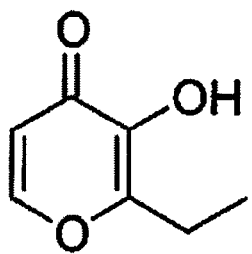
FIG. 2. Chemical Structure of Ethyl Maltol Corresponding to a Protonated Molecular Ion [M+H] of 141 m/z.
Figure 3:
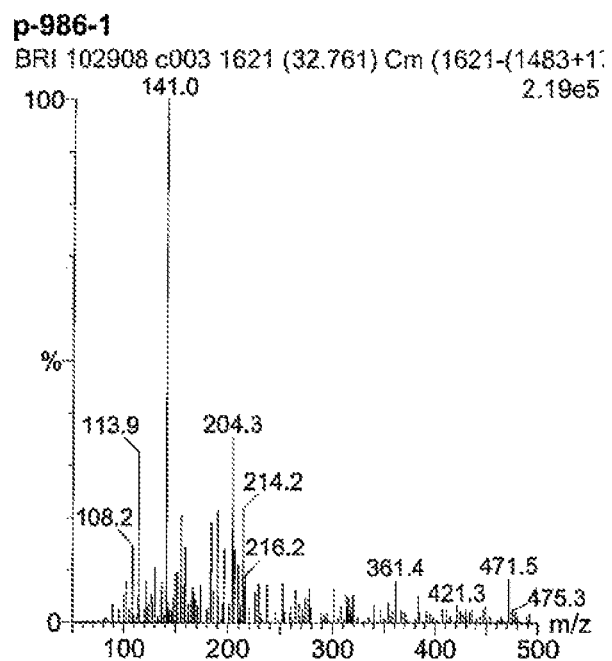
FIG. 3. Representative electrospray mass spectrum of ethyl maltol at a molecular ion [M+H] of 141 m/z was observed from the reference standard sample P-986-1.

The chemical structure of ethyl maltol is presented in FIG. 2. The corresponding mass spectrum of ethyl maltol obtained from the reference standard sample P-986-1 at the nominal retention time of 33 minutes is presented in FIG. 3, showing an expected protonated molecular ion at 141 m/z.

Figure 4:
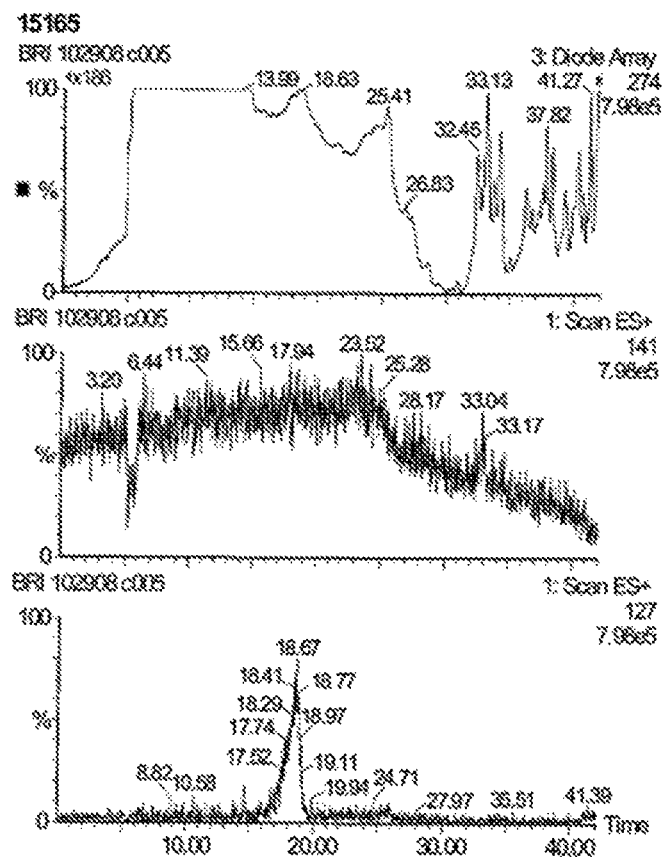
FIG. 4. The HPLC/UV 274 nm chromatogram of test sample 15165 (Top). The corresponding LC/MS selected-ion chromatogram of the ethyl maltol protonated molecular ion [M+H] of 141 m/z at a nominal retention time of 33 minutes (Middle), and the corresponding LC/MS selected-ion chromatogram of the maltol protonated molecular ion [M+H] of 127 m/z at a nominal retention time of 19 minutes (Bottom).
Figure 5:
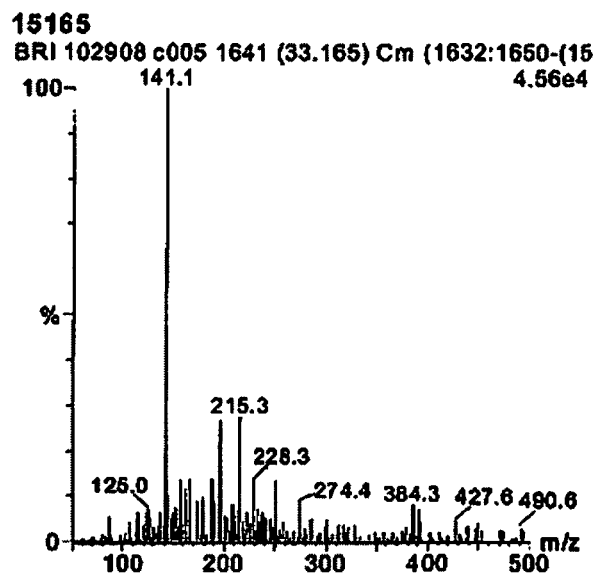
FIG. 5. Representative electrospray mass spectrum of ethyl maltol at a molecular ion [M+H] of 141 m/z was observed from the nominal retention time of 33 minutes in the selected-ion chromatogram of test sample 15165.

A representative LC/MS selected-ion chromatogram of test sample 15165 is presented in FIG. 4, showing a protonated molecular ion [M+H]$^+$ of ethyl maltol at 141 m/z at the nominal retention time of 33 minutes. Maltol was also observed from test sample 15165 at a molecular ion [M+H]$^+$ of 127 m/z at a nominal retention time of 19 minutes. An HPLC ultraviolet detection chromatogram of the test sample 15165 was also simultaneously recorded at UV 274 nm. The corresponding mass spectrum of ethyl maltol from test sample 15165, obtained from the nominal retention time of 33 minutes, is presented in FIG. 5 showing an expected protonated molecular ion at 141 m/z.

Figure 6:
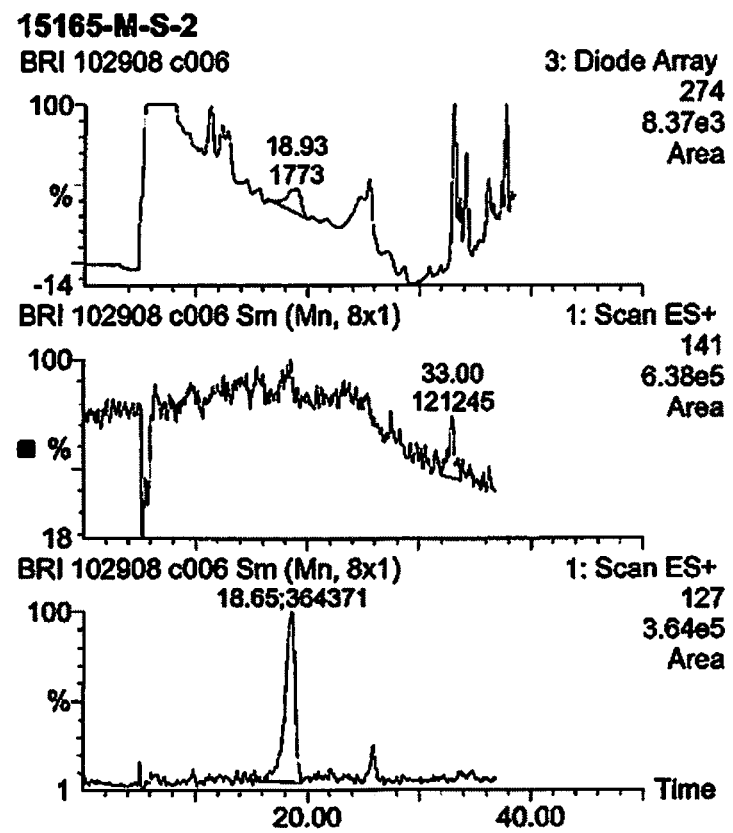
FIG. 6. The HPLC/UV 274 nm chromatogram of test sample 15165-M-S-2 (Top). The corresponding LC/MS selected-ion chromatogram of the ethyl maltol protonated molecular ion [M+H] of 141 m/z at a nominal retention time of 33 minutes (Middle), and the corresponding LC/MS selected-ion chromatogram of the maltol protonated molecular ion [M+H] of 127 m/z at a nominal retention time of 19 minutes (Bottom).
Figure 7:
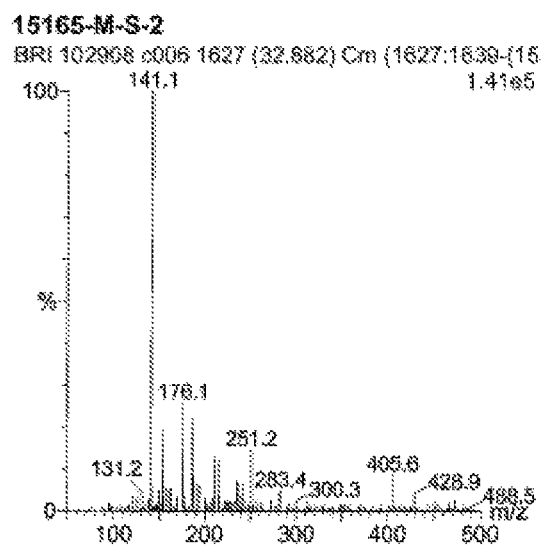
FIG. 7. Representative electrospray mass spectrum of ethyl maltol at a molecular ion [M+H] of 141 m/z was observed from the nominal retention time of 33 minutes in the selected-ion chromatogram of test sample 15165-M-S-2.

A representative LC/MS selected-ion chromatogram of test sample 15165-M-S-2 is presented in FIG. 6, showing a protonated molecular ion [M+H]$^+$ of ethyl maltol at 141 m/z at the nominal retention time of 33 minutes. Maltol was also observed from test sample 15165-M-S-2 at a molecular ion [M+H]$^+$ of 127 m/z at a nominal retention time of 19 minutes. An HPLC ultraviolet detection chromatogram of the test sample 15165-M-S-2 was also simultaneously recorded at UV 274 nm. The corresponding mass spectrum of ethyl maltol from test sample 15165-M-S-2, obtained from the nominal retention time of 33 minutes, is presented in FIG. 7 showing an expected protonated molecular ion at 141 m/z.

Example 6—LC/MS/MS Data Summary

LC/MS/MS experiments were further preformed to provide confirmatory ion fragmentation data on the ethyl maltol peak observed at a nominal retention time of 33 minutes in the two test samples, 15165 and 15165-M-S-2, compared against the corresponding data from the reference standard sample P-986-1. MS/MS data were generated by the use of the first mass spectrometer to isolate the molecular ion of ethyl maltol, followed by inducing fragmentation of ethyl maltol to its structure ion fragments and subsequent detection of the ion fragments (daughter-ions) using a second mass spectrometer operating in tandem.

Figure 8:
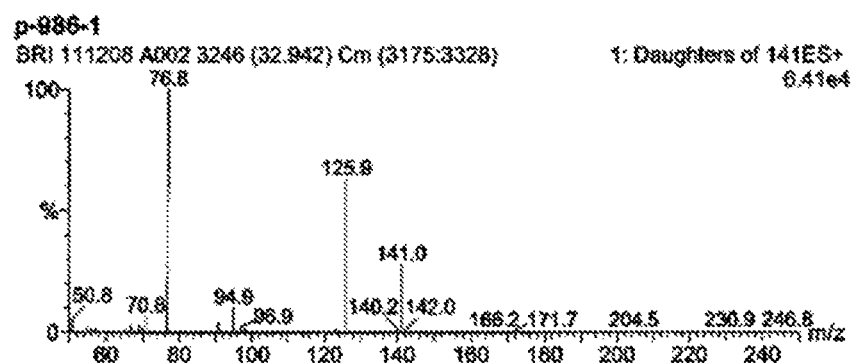
FIG. 8. Representative electrospray daughter-ion mass spectrum of ethyl maltol obtained from the ethyl maltol reference standard sample P-986-1 at a nominal retention time of 33 minutes.

A representative electrospray daughter-ion mass spectrum of the protonated mass ion at 141 m/z obtained from the ethyl maltol reference standard sample P-986-1 at a nominal retention time of 33 minutes is presented in FIG. 8. Daughter ions at 76.8 and 125.9 m/z were indicative of the structure of ethyl maltol.

Figure 9:
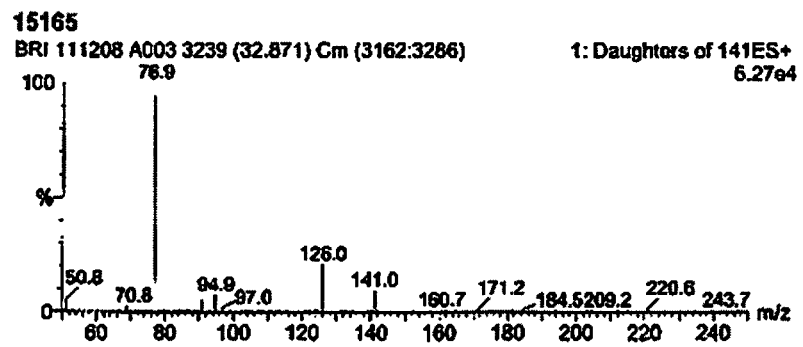
FIG. 9. Representative electrospray daughter-ion mass spectrum of the protonated ion 141 m/z obtained from test sample 15165 at a nominal retention time of 33 minutes revealing the presence of ion fragments at 76.9 and 126.0 m/z as diagnostic fragments of ethyl maltol.

A representative electrospray daughter-ion mass spectrum of the protonated mass ion at 141 m/z obtained from test sample 15165 at a nominal retention time of 33 minutes is presented in FIG. 9. Daughter ions at 76.8 and 125.9 m/z were indicative of the structure of ethyl maltol.

Figure 10:
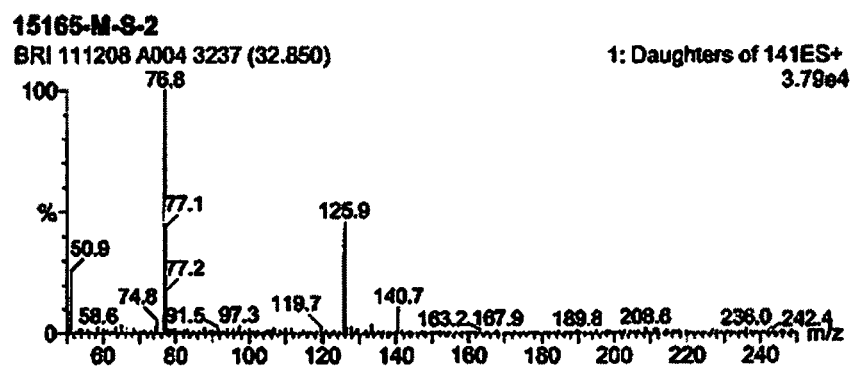
FIG. 10. Representative electrospray daughter-ion mass spectrum of the protonated ion 141 m/z obtained from test sample 15165-M-S-2 at a nominal retention time of 33 minutes revealing the presence of ion fragments at 76.9 and 126.0 m/z as diagnostic fragments of ethyl maltol.

A representative electrospray daughter-ion mass spectrum of the protonated mass ion at 141 m/z obtained from test sample 15165-M-S-2 at a nominal retention time of 33 minutes is presented in FIG. 10. Daughter ions at 76.8 and 125.9 m/z were indicative of the structure of ethyl maltol.

LC/MS and LC/MS/MS data from the assay of blank solvent between sample analyses were observed to be freed from chromatographic and mass carry-over and interference.

Based on LC/MS and LC/MS/MS evidence relating to the retention times, the molecular ion, and ion fragmentation information, the two test samples 15165 and 15165-M-S-2 were both confirmed to contain ethyl maltol with reference against the corresponding data from an ethyl maltol reference standard.

While the preferred embodiments of the invention have been described above, it will be recognized and understood that various modifications may be made therein, and the appended claims are intended to cover all such modifications which may fall within the spirit and scope of the invention.

The invention claimed is:

1. A method for ethyl maltol extraction and isolation comprising:
    drying passionflower plant parts;
    grinding the dried passionflower plant parts into a powder;
    extracting the powder with a methanol solvent selected from the group consisting of: dried methanol; 90:10 methanol:water; and methanol, thereby providing an extract;
    eluting ethyl maltol from the extract by size exclusion chromatographic column purification; and
    recovering the eluted ethyl maltol, thereby providing isolated ethyl maltol.

2. The method according to claim 1 wherein the methanol is HPLC grade methanol.

3. The method according to claim 1 wherein the passionflower plant parts are herb tops.

4. The method according to claim 1 wherein the size-exclusion chromatographic column purification is carried out using size exclusion material having an opening of approximately 60 Angstroms.

5. The method according to claim 1 wherein the dried passionflower plant parts are extracted by refluxing.

6. The method according to claim 1 wherein the dried passionflower plant parts are extracted by refluxing for about 4 hours.

* * * * *